(12) United States Patent
Economou et al.

(10) Patent No.: US 7,098,306 B2
(45) Date of Patent: Aug. 29, 2006

(54) METHOD AND COMPOSITIONS FOR TREATING HEPATOCELLULAR CANCER

(75) Inventors: James S. Economou, Pacific Palisades, CA (US); Lisa H. Butterfield, Long Beach, CA (US); Antoni Ribas Bruguera, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 546 days.

(21) Appl. No.: 10/214,725

(22) Filed: Aug. 7, 2002

(65) Prior Publication Data

US 2003/0143237 A1    Jul. 31, 2003

Related U.S. Application Data

(60) Continuation of application No. PCT/US01/04539, filed on Feb. 12, 2001, and a continuation of application No. 09/781,844, filed on Feb. 12, 2001, now abandoned, which is a continuation-in-part of application No. 09/662,505, filed on Sep. 14, 2000, now abandoned, and a continuation-in-part of application No. 09/660,252, filed on Sep. 12, 2000, now abandoned, which is a division of application No. 09/373,913, filed on Aug. 12, 1999, now abandoned, which is a continuation of application No. PCT/US98/02753, filed on Feb. 13, 1998.

(60) Provisional application No. 60/339,690, filed on Dec. 12, 2001, provisional application No. 60/181,966, filed on Feb. 10, 2000, provisional application No. 60/038,375, filed on Feb. 13, 1997.

(51) Int. Cl.
*C07K 7/06* (2006.01)

(52) U.S. Cl. ............ 530/328; 514/15; 424/185.1; 424/277.1

(58) Field of Classification Search ........... 530/300, 530/328; 514/2, 15; 424/185.1, 277.1
See application file for complete search history.

(56) References Cited

FOREIGN PATENT DOCUMENTS

| EP | 0353 814 A | 2/1990 |
|---|---|---|
| JP | 2005866 A | 1/1990 |
| JP | A H2-218694 | 8/1990 |
| WO | WO 96/22787 | 8/1998 |

OTHER PUBLICATIONS

Database UniProtKB Accession No. P02771 (printed from the Internet on Feb. 1, 2006), 6 pp.*
Butterfield et al. (Expert Opin. Biol. Ther. 2002; 2 (2): 123-133).*
Lollini et al. (Curr. Cancer Drug Targets. May 2005; 5 (3): 221-228).*
Lollini et al. (Trends Immunol. Feb. 2003; 24 (2): 62-66).*
Abelev et al. (Semin. Cancer Biol. Apr. 1999; 9 (2): 95-107).*
Wang et al. (Exp. Opin. Biol. Ther. 2001; 1 (2): 277-290).*
Bodey et al. (Anticancer Research. 2000; 20: 2665-2676).*
Cox et al. (Science. 1994; 264: 716-719).*
Ezzell (Journal of NIH Research. 1995; 7: 46-49).*
Spitler (Cancer Biotherapy. 1995; 10: 1-3).*
Boon (Advances in Cancer Research. 1992; 58: 177-210).*
Arceci (Journal of Molecular Medicine. 1998; 76: 80-93).*
Lee et al. (Journal of Immunology. 1999; 163: 6292-6300).*
Zaks et al. (Cancer Research. 1998; 58: 4902-4908).*
Gao et al. (Journal of Immunotherapy. 2000; 23: 643-653).*
Hu et al. (Cancer Research. 1996; 56: 2479-2483).*
Jaeger et al. (International Journal of Cancer. 1996; 66: 162-169).*
Mukherji et al. (Proceedings of the National Academy of Science USA. 1995; 92: 8078-8082).*
Bocchia et al. (Haematologica. 2000; 85; 1172-1206).*
Gura (Science. 1997; 278: 1041-1042).*
Reilly et al. (Curr. Opin. Investig. Drugs. Jan. 2001; 2 (1): 133-135).*
Butterfield, L.H., et al.: "T cell responses to HLA-A* 0201-Restricted Peptides Derived from Human 'alpha! fetoprotein" Journal of Immunology Apr. 15, 2001 United States, vol. 166, No. 8, Apr. 15, 2001, pp. 5300-5308, XP002235963 ISSN: 0022-1767.
Morinaga T. et al., "Primary Structures of Human α-fetoprotein and Its MRNA," *Proc. Natl. Acad. Sci. USA*, 80 (15), pp. 4604-4608 (1983).
Kazuo Sato et al., "Research on α-fetoprotein (VII)," *Nihon University Journal of Medicine*, 43 (10), pp. 835-842 (1984).
Hidematsu Hirai, "Diagnosis and Treatment of Liver Cancer by α-fetoproteins," *Seibutsu Butsuri Kagaku*, 28 (6), pp. 333-341 (1984).
Taga, H., "The Effect of Active Immunization of Rats with Heterologous α-fetoprotein upon Hepatocarcinogenesis Induced by 3'-methyl-4-dimethylaminobenzene," *Gann*, 74 pp. 1 248-257(1983).

* cited by examiner

*Primary Examiner*—Stephen L. Rawlings
(74) *Attorney, Agent, or Firm*—David A. Farah; Sheldon & Mak

(57) ABSTRACT

A method for preventing or for treating cancer in a mammal, where the cancer cells express at least a part of an alpha fetoprotein molecule at the cell surface. The method comprises creating an immune response in the mammal to at least part of the amino acid sequence of an alpha fetoprotein molecule, where the immune response comprises activating alpha fetoprotein peptide specific T lymphocytes against the cancer cells, and where the part of the alpha fetoprotein molecule is selected from the group consisting of residues 137–145 of SEQ ID NO:2, and residues 325–334 of SEQ ID NO:2 and a combination of the preceeding.

2 Claims, No Drawings

METHOD AND COMPOSITIONS FOR TREATING HEPATOCELLULAR CANCER

CROSS-REFERENCE TO RELATED APPLICATION

The present application claims the benefit of U.S. patent appplication Ser. No. 60/339,690, filed Dec. 12, 2001; and the present application is a continuation of U.S. patent application Ser. No. 09/781,844, filed Feb. 12, 2001, now abandoned, which claims the benefit of U.S. Provisional Patent Application No. 60/181,966, filed Feb. 10, 2000; and the present application is a continuation of PCT Patent Application PCT/US01/04539, filed Feb. 12, 2001, which is a continuation-in-part of U.S. patent application Ser. No. 09/662,505, filed Sep. 14, 2000, now abandoned, and U.S. patent application Ser. No. 09/660,252, filed Sep. 12, 2000, now abandoned, which are divisional applications of U.S. patent application Ser. No. 09/373,913, filed Aug. 12, 1999, now abandoned, which is a continuation of PCT/US98/02753, filed Feb. 13, 1998, which claims the benefit of U.S. patent application Ser. No. 60/038,375, filed Feb. 13, 1997; and the contents of all of which are incorporated by reference herein in their entirety.

STATEMENT REGARDING FEDERALLY SPONSORED RESEARCH OR DEVELOPMENT

This invention was made with United States Government support under subcontract number NIH/NCI ROI CA 77623. The United States Government has certain rights in this invention.

BACKGROUND

Primary liver cancer is a major cause of cancer deaths worldwide. Hepatocellular carcinoma (HCC) is the most common type of primary liver cancer, having a global incidence of approximately 1.2 million cases per year. In some areas of the world, such as Southeast Asia and Sub-sahara Africa, hepatocellular carcinoma is one of the most common types of malignancies. The high frequency of the disease appears to be related to the high incidence of viral hepatitis in these regions.

Curative therapy of hepatocellular carcinoma is currently limited to individuals with nonmetastatic disease and involves surgical resection of the tumor with or without liver transplantation. Even surgical resection and transplantation, however, do not cure most tumors because of recurrence after resection. Chemotherapeutic approaches to treatment have been largely ineffective.

Therefore, there remains a need for an effective treatment for hepatocellular carcinoma. The treatment should ideally be suitable for use in lesser developed countries that have the highest incidence of the disease. Further, the treatment should be appropriate for use in individuals with unresectable tumors and with metastatic disease.

SUMMARY

In one embodiment, the present invention is a method for preventing or for treating cancer in a mammal, where the cancer cells express at least a part of an alpha fetoprotein molecule at the cell surface. The method comprises the step of creating an immune response in the mammal to at least part of the amino acid sequence of an alpha fetoprotein molecule where the immune response comprises activating alpha fetoprotein peptide specific T lymphocytes against the cancer cells. In one embodiment, the alpha fetoprotein peptide specific T lymphocytes are cytotoxic T lymphocytes. In a preferred embodiment, the alpha fetoprotein molecule is SEQ ID NO:2. In a particularly preferred embodiment, the alpha fetoprotein molecule is selected from the group consisting of residues 137–145 of SEQ ID NO:2, residues 158–166 of SEQ ID NO:2, residues 325–334 of SEQ ID NO:2 and residues 542–550 of SEQ ID NO:2. In one embodiment, the cancer is hepatocellular carcinoma. In another embodiment, the mammal is a human.

In a preferred embodiment, the step of creating an immune response comprises administering to the mammal one or more than one composition including a peptide comprising at least part of the alpha fetoprotein amino acid sequence. In a particularly preferred embodiment, the peptide is selected from the group consisting of residues 137–145 of SEQ ID NO:2, residues 158–166 of SEQ ID NO:2, residues 325–334 of SEQ ID NO:2, and residues 542–550 of SEQ ID NO:2. In another preferred embodiment, the peptide is selected from the group consisting of residues 1–9 of SEQ ID NO:2, residues 178–186 of SEQ ID NO:2, residues 218–226 of SEQ ID NO:2, residues 235–243 of SEQ ID NO:2, residues 306–315 of SEQ ID NO:2, residues 485–493 of SEQ ID NO:2, residues 492–500 of SEQ ID NO:2, residues 507–516 of SEQ ID NO:2, residues 547–556 of SEQ ID NO:2 and residues 555–563 of SEQ ID NO:2.

In another preferred embodiment, the step of creating an immune response comprises administering to the mammal one or more than one composition including dendritic cells pulsed with one or more than one peptide that forms at least part of the amino acid sequence of SEQ ID NO:2. In yet another preferred embodiment, the step of creating an immune response comprises administering to the mammal one or more than one composition including dendritic cells transduced with a recombinant adenoviral vector encoding alpha fetoprotein.

In another embodiment, the present invention is a method for preventing or for treating hepatocellular carcinoma in a human, where the cancer cells express at least a part of an alpha fetoprotein molecule at the cell surface, the method comprising the step of activating alpha fetoprotein cytotoxic T lymphocytes against the cancer cells to at least part of the amino acid sequence of SEQ ID NO:2 by administering to the human one or more than one composition including a peptide selected from the group consisting of residues 137–145 of SEQ ID NO:2, residues 158–166 of SEQ ID NO:2 and residues 325–334 of SEQ ID NO:2.

In another embodiment, the present invention is a method for preventing or for treating hepatocellular carcinoma in a human, where the cancer cells express at least a part of an alpha fetoprotein molecule at the cell surface, the method comprising the step of activating alpha fetoprotein cytotoxic T lymphocytes against the cancer cells to at least part of the amino acid sequence of SEQ ID NO:2 by administering to the human one or more than one composition including a peptide selected from the group consisting of residues 542–550 of SEQ ID NO:2.

In another embodiment, the present invention is a method for preventing or for treating hepatocellular carcinoma in a human, where the cancer cells express at least a part of an alpha fetoprotein molecule at the cell surface, the method comprising the step of activating alpha fetoprotein cytotoxic T lymphocytes against the cancer cells to at least part of the amino acid sequence of SEQ ID NO:2 by administering to the human one or more than one composition including a peptide selected from the group consisting of residues 1–9 of SEQ ID NO:2, residues 178–186 of SEQ ID NO:2, residues 218–226 of SEQ ID NO:2, residues 235–243 of SEQ ID NO:2, residues 306–315 of SEQ ID NO:2, residues 485–493 of SEQ ID NO:2, residues 492–500 of SEQ ID NO:2, residues 507–516 of SEQ ID NO:2, residues 547–556 of SEQ ID NO:2 and residues 555–563 of SEQ ID NO:2.

In another embodiment, the present invention is a method for preventing or for treating hepatocellular carcinoma in a human, where the cancer cells express at least a part of an alpha fetoprotein molecule at the cell surface, the method comprising the step of activating alpha fetoprotein cytotoxic T lymphocytes against the cancer cells to at least part of the amino acid sequence of SEQ ID NO:2 by administering to the human one or more than one composition including dendritic cells pulsed with one or more than one peptide that forms at least part of the amino acid sequence of SEQ ID NO:2. The one or more than one peptide is selected from the dendritic cells pulsed with one or more than one peptide is selected from the group consisting of residues 137–145 of SEQ ID NO:2, residues 158–166 of SEQ ID NO:2, residues 325–334 of SEQ ID NO:2, and residues 542–550 of SEQ ID NO:2.

In another embodiment, the present invention is a method for preventing or for treating hepatocellular carcinoma in a human, where the cancer cells express at least a part of an alpha fetoprotein molecule at the cell surface, the method comprising the step of activating alpha fetoprotein cytotoxic T lymphocytes against the cancer cells to at least part of the amino acid sequence of SEQ ID NO:2 by administering to the human one or more than one composition including dendritic cells transduced with a recombinant adenoviral vector encoding alpha fetoprotein.

In another embodiment, the present invention is an isolated peptide useful for preventing or for treating cancer selected from the group consisting of residues 137–145 of SEQ ID NO:2, residues 158–166 of SEQ ID NO:2, and residues 325–334 of SEQ ID NO:2. In a preferred embodiment, the present invention is a composition for preventing or for treating cancer comprising one or more than one peptide selected from the group consisting of residues 137–145 of SEQ ID NO:2, residues 158–166 of SEQ ID NO:2, and residues 325–334 of SEQ ID NO:2 in an amount sufficient to create an immune response to alpha fetoprotein in a mammal. The composition can additionally comprise an adjuvant. In another embodiment, the present invention is a method for preventing or for treating cancer in a human comprising the step of administering to the human one of these peptides or one of these compositions.

The present invention also includes means for preventing or for treating cancer comprising one or more than one peptide selected from the group consisting of residues 137–145 of SEQ ID NO:2, residues 158–166 of SEQ ID NO:2, residues 325–334 of SEQ ID NO:2 and residues 542–550 of SEQ ID NO:2.

In another embodiment, the present invention is an isolated peptide useful for preventing or for treating cancer having a sequence according to residues 542–550 of SEQ ID NO:2. In a preferred embodiment, the present invention is a composition for preventing or for treating cancer comprising a peptide having a sequence according to residues 542–550 of SEQ ID NO:2. The composition can additionally comprise an adjuvant. In another embodiment, the present invention is a method for preventing or for treating cancer in a human comprising the step of administering to the human this peptide or one of these compositions.

The present invention also includes means for preventing or for treating cancer comprising a peptide having a sequence according to residues 542–550 of SEQ ID NO:2.

DESCRIPTION

In one embodiment, the present invention is a group of peptides that, alone or in combination, can be used to treat hepatocellular carcinoma. In another embodiment, the present invention is a method for preventing or for treating hepatocellular carcinoma by administering one or more than one peptide of the present invention, alone or in combination, or a composition comprising one or more than one peptide of the present invention. In another embodiment, the present invention is a method for preventing or for treating hepatocellular carcinoma by administering dendritic cells pulsed with one or more than one peptide of the present invention, or transduced with a recombinant adenoviral (AdV) vector encoding alpha fetoprotein.

Approximately 80% of hepatocellular carcinomas reactivate alpha fetoprotein expression. Both the murine and human T cell repertoires can recognize AFP-derived peptide epitopes in the context of MHC class I. Therefore, despite being exposed to high plasma levels of this oncofetal protein during embryonic development, not all of AFP-specific T cells are deleted during the ontogeny of the immune system.

The present invention involves the determination of the identity of peptides derived from human alpha fetoprotein, SEQ ID NO:2, which when presented in the context of HLA-A*0201, are recognized by the human T cell repertoire. As summarized in Table 1, below, four AFP-derived peptides were identified and designated the "dominant" peptides. They are PLFQVPEPV, $hAFP_{137-145}$, residues 137–145 of SEQ ID NO:2; FMNKFIYEI, $hAFP_{158-166}$, residues 158–166 of SEQ ID NO:2; GLSPNLNRFL, $hAFP_{325-334}$, residues 325–334 of SEQ ID NO:2; and GVALQTMKQ, $hAFP_{542-550}$, residues 542–550 of SEQ ID NO:2. Each possesses one or two anchor residues.

Each of the dominant peptides stabilized HLA-A*0201 on T2 cells in a concentration-dependent class I binding assay. The peptides were stable for 2 to 6 hours in an off-kinetics assay. Additionally, each dominant peptide induced peptide-specific T cells in vitro from several normal HLA-A*0201 donors. Importantly, these hAFP peptide-specific T cells were also capable of recognizing HLA-A*0201+/AFP positive tumor cells in both cytotoxicity assays and IFNg ELISPOT assays. This information is summarized

TABLE 1

SUMMARY OF THE DOMINANT PEPTIDES

| Peptide | Location in SEQ ID NO: 2 | Sequence | Anchors | T2 binding concentration | Relative Off kinetics |
|---|---|---|---|---|---|
| $hAFP_{137-145}$ | 137–145 | PLFQVPEPV | 2 | 2.5 mM | 4 hours |
| $hAFP_{158-166}$ | 158–166 | FMNKFIYEI | 2 | 0.5 mM | 4 hours |

TABLE 1-continued

SUMMARY OF THE DOMINANT PEPTIDES

| Peptide | Location in SEQ ID NO: 2 | Sequence | Anchors | T2 binding concentration | Relative Off kinetics |
|---|---|---|---|---|---|
| hAFP$_{325-334}$ | 325–334 | GLSPNLRFL | 2 | 10 mM | 2 hours |
| hAFP$_{542-550}$ | 542–550 | GVALQTMKQ | 1 | >100 mM | 6 hours |

As demonstrated in the present invention, activation of these T cells can be achieved by presenting these dominant peptides in an immunostimulatory context, including presentation by professional antigen presenting dendritic cells. Dendritic cells transduced with a recombinant adenoviral (AdV) vector encoding alpha fetoprotein cDNA, SEQ ID NO: 1, will process and present the four dominant peptide epitopes in the context of MHC, and will also induce AFP-specific T cell activation. Similarly immunized HLA-A*0201/K$^b$ mice also recognized AFP peptide-pulsed cells in cytokine release assays. Further, AFP peptide-stimulated human and HLA-A*0201/K$^b$ mouse T cell responses recognized hAFP-engineered targets and, to a lesser extent, naturally AFP-expressing human hepatocellular carcinoma cells. Finally, mass spectrometry was used to identify at least three AFP epitopes from complex mixtures of peptides eluted from HLA-A*0201+ HCC cells. Thus, multiple lines of evidence are provided that each of these four dominant peptides is immunogenic and naturally processed and presented in the context of HLA-A*0201.

Ten other peptides, designated "subdominant" peptides, were identified that had either weak or less reproducible responses but were positive in more than one type of assay. These ten peptides are MKWVESIFL, residues 1–9 of SEQ ID NO:2; ILLWAARYD, residues 178–186 of SEQ ID NO:2; LLNQHACAV, residues 218–226 of SEQ ID NO:2; FQAITVTKL, residues 235–243 of SEQ ID NO:2; TTLERGQCII, residues 306–315 of SEQ ID NO:2; CIRHEMTPV, residues 485–493 of SEQ ID NO:2; PVNPGVGQC, residues 492–500 of SEQ ID NO:2; NRRPCFSSLV, residues 507–516 of SEQ ID NO:2; TMKQEFLINL, residues 547–556 of SEQ ID NO:2; and NLVKQKPQI, residues 555–563 of SEQ ID NO:2.

Though the compositions and methods of the present invention are disclosed primarily in the context of using one or more than one of the dominant peptides, hAFP$_{137-145}$, residues 137–145 of SEQ ID NO:2; hAFP$_{158-166}$, residues 158–166 of SEQ ID NO:2; hAFP$_{325-334}$, residues 325–334 of SEQ ID NO:2; and hAFP$_{542-550}$, residues 542–550 of SEQ ID NO:2, it is within the scope of the present invention to use one or more than one of the ten subdominant peptides in place or in conjunction with one or more than one of the four dominant peptides.

The identification of the dominant peptides and subdominant peptides will now be discussed in greater detail. First, peptide sequences from hAFP, SEQ ID NO:2, (Genbank accession numbers: J00077, J00076 and V01514) were identified that would potentially bind to HLA-A*0201. These peptides have between nine or ten amino acids in length, the amino acids isoleucine, leucine and methionine in position 2, or can have the amino acids isoleucine, leucine and valine in peptide positions 9 or 10, depending on the peptide length, or both. Seventy-four such peptides were identified using the University of Wisconsin Genetics Computer Group Program "find patterns" to screen the hAFP sequence, SEQ ID NO:2. Each of the 74 peptides were synthesized using standard techniques.

Each of the 74 peptide candidates were tested for concentration dependent binding to T2 cells in an HLA-A*0201 stabilization assay. T2 (TAP deficient) cells that had been incubated at room temperature the previous night to increase cell surface MHC class I molecule expression were then incubated overnight with each peptide over a range of peptide concentrations, from 0.1 mM-100 mM. Stability of HLA-A*0201 was assayed by flow cytometry after staining the cells with anti-HLA-A2 antibody (BB7.2) and goat antimouse-FITC. The HLA-A*0201 strongly binding Flu matrix peptide (aa 58–66) (Flu) was used as a positive control.

Next, MHC-peptide complex stability was determined using an off-kinetics assay. HLA-A*0201 LCL were stripped with a mild pH3.2 citrate-phosphate acid buffer. Each peptide was immediately pulsed onto cells at 200 mM for 1 hour in the presence of b2 microglobulin at 3 ug/ml at room temperature. Excess peptide was washed off and the cells were incubated at 37° C. for 0, 2, 4 and 6 hours. Cells were washed at the end of each time point and stained for cell surface HLA-A2 expression, then analyzed by flow cytometry. The peptide-MHC class I complex was considered stable if the mean fluorescence intensity increased at least 1.5-fold from cells that were stripped but not pulsed with peptide. All four dominant peptides were stable for 2 to 6 hours in the off-kinetics assay.

The four dominant peptides were then subjected to additional immunological and physicochemical studies. These studies included in vitro studies where (1) peptides were used to make AFP peptide-specific human T cell cultures which were both peptide specific and recognized native AFP-expressing cells; (2) AdVhAFP-transduced dendritic cells were used to make AFP specific human T cells which recognized AFP positive cells, as well as AFP negative cells pulsed with the dominant peptides; and in vivo studies where (1) transgenic mice which were immunized with peptides had splenocytes that recognized peptides and AFP positive cells; and (2) AdVhAFP/DC immunized mice recognized AFP positive cells and as well as AFP negative cells pulsed with the dominant peptides. These studies showed that the dominant peptides are immunogenic, that AFP itself is immunogenic, that the dominant peptides are naturally processed and presented on the surface of AFP positive cells and that both AFP/DC or the dominant peptides can be used to generate AFP-specific T cells which make cytokines and kill AFP positive cells. Further, mass spectroscopy was used to physically identify the AFP peptides from the surface of AFP positive hepatocellular carcinoma cells.

First, repetitive peptide stimulation of naive HLA-A*0201 human T cell cultures was performed to demonstrate peptide immunogenicity in the context of the human T cell repertoire and the ability of peptide-specific T cells to recognize AFP-transfected targets. Bulk T cell cultures were generated from PBMC pulsed with each dominant AFP-derived peptide (supplemented with KLH, IL-7 and IL-2) and were tested between weeks 3 and 7 of expansion for the ability to recognize both peptide-pulsed and AFP-expressing targets. These cultures expanded peptide-specific T cells, as evidenced by the ability to secrete IFNg upon recognition of specific peptide-pulsed JY cells and not control MART-$1_{27\text{-}35}$ pulsed JY in the ELISPOT assay. The AFP peptide-specific bulk T cells also recognized both AFP negative stably transfected and AdVhAFP-transduced HLA-A*0201 melanoma cells (M202) compared to unmodified or empty AdVRR5 transduced parental cells as shown by an increased frequency of IFNg-producing AFP-specific T cells. In order to assess the ability to recognize the HLA-A*0201+, naturally AFP-expressing hepatocellular carcinoma cell line HepG2 (compared to the HLA-A2−/AFP positive HCC line Hep3B), both cytotoxicity and ELISPOT assays were performed.

Additionally, CTL were generated from AdV transduced dendritic cells. Briefly, dendritic cells prepared from PBMC incubated with GM-CSF and IL-4 were transduced with AdVhAFP or AdVMART1 at a multiplicity of infection (moi) of 1,000 for 2 hours. Transduced dendritic cells were washed, irradiated and plated at $1–2\times10^5$ cells/ml to serve as stimulators for CTL generation. Autologous non-adherent cells were depleted of CD4, CD14, CD19 and CD56+ cells by magnetic bead depletion to prepare CD8+ enriched responder cells (population generally 80% CD8+, not shown). The CD8+ cells were plated with the transduced dendritic cells at $2\times10^6$ cells/ml, in 5% autologous medium plus IL-7 at 10–25 ng/ml. Cultures were supplemented with IL-2 at 10 U/ml every 3–4 days. The CD8+ CTL were restimulated weekly with fresh, autologous AdV-transduced dendritic cells at a ratio of 1 dendritic cell to 10–20 CD8+ CTL. Most cultures were phenotyped for CD4+ and CD8+ cells on a weekly basis. Each dominant peptide induced peptide-specific T cells in vitro from several normal HLA-A*0201 donors.

Because AdVhAFP/DC in vitro stimulated human T cells specifically recognized hAFP-transfected targets in both CTL and ELISPOT assays, the four dominant peptides were next studied to determine whether they were specifically recognized by the AdVhAFP/DC stimulated T cells. After 7 to 21 days of culture, CD8-enriched T cells stimulated weekly with AdVhAFP/DC were tested for both cytotoxicity and the frequency of hAFP peptide-specific IFNg cytokine producing cells. AdVhAFP/DC T cell cultures were cytotoxic for JY cells pulsed with each of the four AFP peptides, indicating that CTL to these peptides could be expanded from peripheral blood of normal donors. After restimulation with autologous peptide pulsed LCL or JY cells, these bulk cultures also contained a much higher frequency of IFNg-secreting cells specific for AFP peptides compared to MART-$1_{27\text{-}35}$, indicating that, in addition to hAFP$_{542\text{-}550}$, the three other dominant peptides are also naturally processed and presented by AdVhAFP-transduced dendritic cells.

The AdVhAFP/DC stimulated T cell cultures also had a low frequency of cytokine-producing cells which recognized the A*0201+/AFP positive hepatocellular carcinoma line HepG2 but not the A*0201−/AFP positive HCC line Hep3B. T lymphocytes synthesizing the Th1 cytokines IFNg and TNFa were detected, while the Th2 cytokine IL-4 was not detected. IL-10 was also detected when the hepatocellular carcinoma lines were plated without T cells, indicating that production of this cytokine was tumor cell-derived.

The HLA-A*0201/K$^b$ transgenic mice were used to screen the 74 peptides to determine whether any of these peptides were immunogenic, and naturally processed and presented in the context of HLA-A*0201 as follows. HLA-A*0201/K$^b$ transgenic female mice were originally purchased from Harlan-Sprague Dawley (Indianapolis, IN US), and are currently bred by the animal facility of the Dept. of Radiation Oncology at University of California, Los Angeles.

For peptide immunizations, mice received 100 μg AFP or control peptide emulsified 1:1 in complete Freund's adjuvant subcutaneously. After immunization with each peptide emulsified in complete Freund's adjuvant, draining lymph node cells produced IFNg upon recognition of cells stably transfected with hAFP. Furthermore, alpha fetoprotein peptide-specific T cells could be identified in the spleens of mice immunized with dendritic cells transduced with an AFP-expressing adenovirus (AdVhAFP). Thus, the four dominant peptides are naturally processed and presented in the context of class I and are immunogenic.

Next, the in vivo immunogenicity of these four dominant peptides were confirmed. HLA-A*0201/K$^b$ mice were immunized with each dominant peptide pulsed onto syngeneic dendritic cells. IFNg specific ELISPOT assays were performed with splenocytes restimulated in vitro with either the immunizing dominant peptide (or MART-1 peptide) or with Jurkat/AFP or Jurkat/MART transfected cell lines. Immunization with each hAFP peptide and subsequent restimulation with either peptide or Jurkat/AFP induced large numbers of AFP-specific IFNg-producing cells. Lymphocytes from PBS injected mice showed neither cytotoxicity nor IFNg production regardless of restimulation. Mice immunized with MART-$1_{27\text{-}35}$ peptide produced MART-1 specific responses but no AFP peptide responses.

Then, dendritic cells were prepared from bone marrow progenitors by differentiation in GM-CSF and IL-4 and were transduced with a recombinant AdV vector (AdVhAFP) that included hAFP cDNA. SEQ ID NO: 1. In vitro cultured dendritic cells were transduced in RPMI/2% FCS at an moi of 100. Transduction was carried out for two hours at 37° C. The dendritic cells were then washed and resuspended at $5\times10^5$ dendritic cells per 0.2 ml PBS per animal for injection. In all cases viability exceeded 95%. Two weeks after immunization, splenocytes from mice were restimulated with Jurkat cells stably transfected with hAFP (Jurkat/AFP) or with MART-1 (Jurkat/MART). The frequency of AFP-specific vs. MART-1 specific IFNg-release was determined by ELISPOT averaging three independent experiments where p<0.02. Cytotoxicity was assayed against Jurkat/AFP and Jurkat/MART in a 5 hour $^{51}$Cr-release assay.

Next, HPLC and mass spectrometric identification was performed on the dominant peptides eluted from an HLA-A*0201 human hepatocellular carcinoma line. A summary of the results of these analyses are present in Table 2, below.

To elute peptides, HepG2 and Hep3B cells were washed three times with PBS before being incubated with 5 ml of citrate-phosphate buffer at pH 3.2 for 1 minute. The suspension was centrifuged (800×g for 5 minutes) and a total of 500 ml of cell-free supernatant was collected for each cell line. The materials were lyophilized to dryness and stored at −20° C.

Lyophilized materials were redissolved in 30 ml of water/acetonitrile/triflouroacetic acid (W/A/TFA, 95/5/0.1 all by vol.). This solution was pumped onto an analytical reverse phase HPLC column (Keystone Scientific C$_{18}$ Betasil, 250 mm×2 mm, 5 mm particle size, 100 Å pore size) equilibrated in W/A/TFA, at a flow rate of 0.2 ml/min. The column was eluted using an increasing linear gradient of 0.1% TFA in acetonitrile (time/%acetonitrile=0/5, 5/5, 55/100, 60/100). Column eluate absorbance was monitored at 215 and 280 nm and 1 minute fractions were collected. The retention times of the synthetic peptides with amino acid sequences corresponding to the immunostimulatory peptides were obtained using the same separation gradient on a separate column.

MALDI-TOF mass spectrometry was performed to analyze HPLC fractionated peptides acid-eluted from the AFP producing hepatocellular carcinoma cell lines HepG2 (HLA-A2$^+$) and Hep3B (HLA-A2$^-$). A Voyager-REACTION PRODUCTS (PerSeptive Biosystems, Framingham, Mass.) Matrix Assisted Laser Desorption Ionization/Time-Of-Flight (MALDI-TOF) instrument was used to acquire the mass spectra. The instrument uses a stainless-steel target, on which the samples are deposited and dried. All spectra were externally calibrated with insulin, resulting in mass accuracy typically within ±0.1%. Lyophilized HPLC fractions were resuspended in 10 μl of 70% acetonitrile with 0.1% TFA. One μl of this material was spotted along with 1 μl of the matrix a-cyano-4-hydroxycinnamic acid (Sigma, 10 mg/ml in 70% ACN/0.1% TFA). Spectra were obtained by scanning from m/z 500–7000.

The MALDI analysis of the HPLC fractions established that almost all fractions contained up to 20 different peptides in the mass range from 700 to 1500 Da, although frequently with a few dominating signals. Out of this complex mixture, peaks were identified with m/z values corresponding to the calculated monoisotropic protonated molecules ((M+H)$^+$) of hAFP$_{158-166}$, residues 158–166 of SEQ ID NO:2; hAFP$_{325-334}$, residues 325–334 of SEQ ID NO:2; and hAFP$_{542-550}$, residues 542–550 of SEQ ID NO:2 hAFP$_{542-550}$, hAFP$_{158-166}$ and hAFP$_{325-334}$ in the peptide pool eluted from HepG2 cells. A peptide of m/z 975.6 was identified in one HPLC fraction from the HepG2 peptide pool. The calculated (M+H)$^+$ of hAFP$_{542-550}$ was 975.5 and the retention time of the synthetic peptide with amino acids corresponding to hAFP$_{542-550}$, residues 542–550 of SEQ ID NO:2, was 21.2 minutes. Furthermore, no signal at m/z of 975.5±1 was observed in samples with matrix alone and in HPLC fractions 18 to 22 from the Hep3B elution. Similarly, peaks with m/z corresponding to the calculated (M+H)$^+$ of hAFP$_{158-166}$, residues 158–166 of SEQ ID NO:2 and hAFP$_{325-334}$, residues 325–334 of SEQ ID NO:2, were also found in the appropriate fraction derived from HepG2 predicted from the behavior of the standard peptides. These peaks were absent in fractions in the peptide pool eluted from Hep3B. A peak at 1152.2 m/z was observed in one fraction, suggesting the presence of the sodium adduct of hAFP$_{325-334}$, residues 325–334 of SEQ ID NO:2.

Therefore, potential mass candidates were identified for three of the four peptides in the HPLC fractionated peptide pool eluted from the HLA-A*0201 positive HepG2 cells but not from the HLA-A*0201 negative Hep3B cells. In the three peptides that were identified, the peaks were observed in repeated scanning of the spotted samples. A board peak at m/z 1020.9 was observed in one fraction from the HepG2 peptide pool that was beyond the margin of error tolerated by this physicochemical analysis. Therefore, it was not possible to document the presence of hAFP$_{137-145}$, residues 137–145 of SEQ ID NO:2, on the surface of HepG2 cells.

To confirm the presence of dominant peptides in these fractions immunologically, one ml of each HPLC fraction from either HepG2 or Hep3B cells was used to restimulate AdVhAFP/DC immunized murine splenocytes in an ELISPOT assay. 200–250 spots/10$^6$ cells were observed from fractions containing dominant peptides, where 100–130 spots/10$^6$ cells were observed from the other fractions, and a maximum of 50 spots/10$^6$ cells were observed from Hep3B fractions. This further supports the mass spectrometry identification of the dominant peptides.

TABLE 2

| Peptide[1] | HPLC Retention Time of Peptide (min.)[2] | Cal. (M + H)$^{+,[3]}$ | Observed (M + H)$^+$ in HepG2[4] | Observed (M + H)$^+$ in Hep3B[5] | (M + H)$^+$ Identified in HPLC Fraction #[6][6] | Immunologically Reactive Fractions (IFNg ELISPOT)[7] | |
|---|---|---|---|---|---|---|---|
| | | | | | | HepG2 | Hep3B |
| hAFP$_{542-550}$ | 21.2 | 975.5 | 975.6 | None | 21 | 20, 21 | 0 |
| hAFP$_{158-166}$ | 28.9 | 1204.6 | 1204.9 | None | 28 | 27, 28, 29 | 0 |
| hAFP$_{137-145}$ | 28.1 | 1025.6 | None | None | — | 27, 28, 29 | 0 |
| hAFP$_{325-334}$ | 27.7 | 1130.6 | 1130.1 | None | 28 | 27, 28, 29 | 0 |

EXAMPLE I

Method for Preventing or for Treating Hepatocellular Carcinoma by Administering Peptides According to one embodiment of the present invention, there is provided a method for preventing or for treating patients with hepatocellular carcinoma. The method comprises selecting a suitable patient, such as an HLA-A*0201$^+$ patient having AFP positive hepatocellular carcinoma. Next, the patient is administered one or more than one peptide of the present invention. The peptides are administered in a sufficient dose and, preferably, the administration is repeated a plurality of times, to create an immune response to AFP, and thereby creates an immune response to the hepatocellular carcinoma.

In a preferred embodiment, the peptides are a combination of hAFP$_{137-145}$, residues 137–145 of SEQ ID NO:2; hAFP$_{158-166}$, residues 158–166 of SEQ ID NO:2; hAFP$_{325-334}$, residues 325–334 of SEQ ID NO:2; and hAFP$_{542-550}$, residues 542–550 of SEQ ID NO:2. In another preferred embodiment, the one or more than one peptide is administered between 2 times and 5 times. In a particularly preferred embodiment, the peptides are administered 3 times. In another preferred embodiment, the one or more than one peptide is administered three times, at 2:00 week intervals.

In a preferred embodiment, the peptides are administered intradermally, though other routes of administration are suitable as will be understood by those with skill in the art with reference to this disclosure.

In a preferred embodiment, each of the one or more than one peptide is administered emulsified in 0.5 ml of Montanide™ ISA-51, such that when four peptides are combined, they are administered emulsified in a total of 2 ml of Montanide™ ISA-51. The emulsified peptide or peptides are divided into four equal does and each dose is administered in a separate site. In a preferred embodiment, the one or more than one peptide is administered in a dose of between about 50 µg and 2000 µg each. In a preferred embodiment, the one or more than one peptide is administered in a dose of between about 100 µg and 1000 µg each. In a particularly preferred embodiment, the one or more than one peptide is administered in a dose of between about 500 µg.

The method and compositions of the present invention were used to treat several patients with AFP positive/A2.1+ hepatocellular carcinoma. Each of the patients were immunized with the four peptides $hAFP_{137-145}$, residues 137–145 of SEQ ID NO:2; $hAFP_{158-166}$, residues 158–166 of SEQ ID NO:2; $hAFP_{325-334}$, residues 325–334 of SEQ ID NO:2; and $hAFP_{542-550}$, residues 542–550 of SEQ ID NO:2, according to the this method. The peptides were emulsified in 0.5 ml of Montanide™ ISA-51 and combined for a total of 2 ml. The emulsified peptides were divided into four equal doses and each dose was administered in a separate site. Peripheral T cell responses are measured by ELISPOT and tetramer assays. These trials show that the four AFP-derived peptides are immunogenic in vivo, even in patients whose levels of AFP in serum were extremely high before immunization.

The first patient, designated AFP-A1 had a recurrent, unresectable AFP positive/A2.1+ hepatocellular carcinoma. He was administered three immunizations of 100 µg each of the four peptides in Montanide™ ISA at two week intervals. Parallel in vitro PBMC cultures were also established from the first patient's blood before immunization and repetitively pulsed with each peptide. There is clear in vitro recognition of all peptides in day 28 cultures examined by ELISPOT and in 2 of 3 $hAFP_{137-145}$, residues 137–145 of SEQ ID NO:2; and $hAFP_{325-334}$, residues 325–334 of SEQ ID NO:2 but not in $hAFP_{158-166}$, residues 158-166 of SEQ ID NO:2 by tetramer. The presence of $AFP_{542}$-specific T cells could not be assessed by tetramer as an $AFP_{542}$ peptide tetramer could not be folded by the facility where these reagents are prepared. In vivo responses indicated clear recognition of $hAFP_{137-145}$, residues 137–145 of SEQ ID NO:2; $hAFP_{158-166}$, residues 158–166 of SEQ ID NO:2; and $hAFP_{542-550}$, residues 542–550 of SEQ ID NO:2; and a trend towards recognition of $hAFP_{325-334}$, residues 325–334 of SEQ ID NO:2 after the second and third immunization.

The second patient, designated AFP-A2 was a 70 yr old Caucasian male with a history of ethanol-induced liver cirrhosis, who was negative for both Hepatitis B and C. He presented with bloating and was found to have an 8 cm mass in the left lobe of his liver. His AFP level at presentation was 10,400 ng/ml. A liver biopsy revealed a well-differentiated hepatocellular carcinoma in a cirrhotic liver. He was begun on an experimental trial of the antifungal agent FV-462 but had disease progression and ototoxicity. Seven months after presentation, he was then begun on a combination of the four peptides $hAFP_{137-145}$, residues 137–145 of SEQ ID NO:2; $hAFP_{158-166}$, residues 158–166 of SEQ ID NO:2; $hAFP_{325-334}$, residues 325–334 of SEQ ID NO:2; and $hAFP_{542-550}$, residues 542–550 of SEQ ID NO:2 using the protocol according to the present invention. He received two immunizations two weeks apart. Tetramer and ELISPOT data following two immunizations showed that T cell responses were detected to all 4 AFP peptide epitopes.

Therefore, these results indicated that the present method generates a detectible immune response by AFP-specific T cells in patients with advanced hepatocellular carcinoma.

EXAMPLE II

Method for Preventing or for Hepatocellular Carcinoma by Administering Dendritic Cells Pulsed with Peptides of the Present Invention According to one embodiment of the present invention, there is provided a method for preventing or for treating patients with hepatocellular carcinoma. The method comprises selecting a suitable patient, such as an HLA-A*0201+ patient having AFP positive hepatocellular carcinoma. Next, the patient is administered dendritic cells pulsed with one or more than one peptide of the present invention. The dendritic cells are administered in a sufficient dose and, preferably, the administration is repeated a plurality of times, to create an immune response to AFP, and thereby creates an immune response to the hepatocellular carcinoma.

In a preferred embodiment, the dendritic cells are pulsed with a combination of $hAFP_{137-145}$, residues 137–145 of SEQ ID NO:2; $hAFP_{158-166}$, residues 158–166 of SEQ ID NO:2; $hAFP_{325-334}$, residues 325–334 of SEQ ID NO:2; and $hAFP_{542-550}$, residues 542–550 of SEQ ID NO:2. In another preferred embodiment, the dendritic cells are administered between 2 times and 5 times. In a particularly preferred embodiment, the dendritic cells are administered 3 times. In another preferred embodiment, the dendritic cells are administered 3 times, at 2 week intervals.

In a preferred embodiment, the dendritic cells are administered intradermally, though other routes of administration are suitable as will be understood by those with skill in the art with reference to this disclosure. In one embodiment, the dendritic cells are administered in a dose of between about $1 \times 10^5$ and $1 \times 10^8$. In another preferred embodiment, the dendritic cells are administered in a dose of between about $1 \times 10^6$ and $1 \times 10^7$. In a particularly preferred embodiment, the dendritic cells are administered in a dose of about $5 \times 10^6$.

The dendritic cells are prepared from adherent, autologous peripheral blood mononuclear cells exposed for 1 week in tissue culture to granulocyte-macrophage colony stimulating factor (GM-CSF) and interleukin-4 (IL-4), according to techniques known to those with skill in the art. Mononuclear cells are isolated from cells obtained from a single leukapheresis by Ficoll™-Hypaque centrifugation and stored frozen in liquid nitrogen until used to generate dendritic cells. The thawed mononuclear cells are washed once in saline and plated at $2-4 \times 10^7$ cells/25 cm² Costar™ flasks at a concentration of $2.5-5 \times 10^6$ viable cells/ml (RPMI 1640+5% heat-inactivated autologous serum+Gentamycin). After allowing adherence for 2 hours at 37° C., nonadherent cells are removed by washing with saline. Adherent cells are cultured in complete medium for 7 days in the presence of rhGM-CSF (800 U/ml) and rhIL-4 (500 U/ml). Clinical grade GM-CSF was provided by Immunex and IL-4 by Schering-Plough.

Patients undergo a single leukapheresis to obtain at least $2 \times 10^9$ PBL, which is cryopreserved in 70% RPMI 1640, 20% autologous serum and 10% DMSO. Aliquots are thawed at study days −7, 7 and 21. Blood for autologous serum (60 ml) is drawn at the time of leukapheresis and on the day of the first immunization, which is sufficient for the all cell cultures. The AFP-derived immunodominant peptides of the present invention are prepared and purified according to techinques known to those with skill in the art.

Patients are immunized as follows. On the day of immunization, dendritic cells are harvested, washed once in sterile saline solution and resuspended at a concentration an appropriate concentration, such as $10^6$, in 1 mL serum-free RPMI 1640 and 50 mg/ml each of the four immunodomanint peptides separately. After a minimum of one hour of incubation, AFP peptides/DC are pelleted and washed thrice in sterile saline solution. Cells are counted in trypan blue and are resuspended in 0.1 ml sterile saline for intradermal injection.

Before administering the full dose, subjects will receive a skin test with 1/100 of their dose in 0.1 ml of saline. After a 30 minute observation period, they will receive the full dose of AFP peptide-pulsed dendritic cells injected intradermally in 0.1 ml saline in the flank region below the axilla, or below or above the groin. Patients are monitored for 2 hours post-immunization. Preferrably, patients receive pretreatment with 50 mg diphenhydramine and 650 mg of Tylenol™, both orally.

EXAMPLE III

Method for Preventing or for Hepatocellular Carcinoma by Administering Human AFP Adenovirus-Transduced Dendritic Cells According to one embodiment of the present invention, there is provided a method for preventing or for treating patients with hepatocellular carcinoma. The method comprises selecting a suitable patient, such as an HLA-A*0201$^+$ patient having AFP positive hepatocellular carcinoma. Next, the patient is administered human AFP adenovirus-transduced dendritic cells. The dendritic cells are administered in a sufficient dose and, preferably, the administration is repeated a plurality of times, to create an immune response to AFP, and thereby creates an immune response to the hepatocellular carcinoma.

In another preferred embodiment, the dendritic cells are administered between 2 times and 5 times. In a particularly preferred embodiment, the dendritic cells are administered 3 times. In another preferred embodiment, the dendritic cells are administered 3 times, at 2 week intervals.

In a preferred embodiment, the dendritic cells are administered intradermally in the flank region below the axillae or the groin, though other routes of administration are suitable as will be understood by those with skill in the art with reference to this disclosure. In one embodiment, the dendritic cells are administered in a dose of between about $1 \times 10^5$ and $1 \times 10^8$. In another preferred embodiment, the dendritic cells are administered in a dose of between about $1 \times 10^6$ and $1 \times 10^7$. In a particularly preferred embodiment, the dendritic cells are administered in a dose of about $5 \times 10^6$.

Mononuclear cells are isolated from a leukapheresis product by Ficoll™-Hypaque centrifugation and stored in 10% DMSO/20% autologous serum. One week before the DC vaccination, cells are thawed, washed once in PBS and plated at $2-4 \times 10^7$ cells/25 cm$^2$ Costar™ flask at a concentration of $2.5-5 \times 10^6$ viable cells/ml (RPMI 1640+5% heat-inactivated autologous serum). After allowing adherence for 2 hours at 37° C., nonadherent cells are gently removed by washing with PBS. Adherent cells are cultured in complete medium for 7 days in the presence of rhGM-CSF (800 U/ml) and rhIL-4 (500 U/ml). Clinical grade GM-CSF and IL-4 are provided by Schering-Plough.

AdVhAFP is an E1-deleted replication-deficient type 5 adenoviral vector in which the human AFP cDNA is driven by the CMV enhancer/promoter. Viral titers for each final viral production lot are provided based on both genomic DNA quantitation and infectious titer. A ratio in the product of viral particles to biologically active virus of less than 100:1 are deemed acceptable.

Patients are immunized as follows. On the day of immunization, dendritic cells are harvested, washed once in sterile saline solution and resuspended at a concentration of $10^6$–$10^7$ in 1 mL of 2% autologous serum-RPMI 1640 and $10^9$–$10^{10}$ pfu/ml of AdVhAFP (multiplicity of infection=1000:1). After a two-hour incubation at 37° C., AdVhAFP/DC are resuspended in RPMI-1640+5% autologous serum to inactivate non-absorbed adenoviral vector, and then pelleted and washed thrice in sterile saline solution. Cells are counted in trypan blue and the appropriate numbers (between $1 \times 10^5$ and $1 \times 10^8$ depending on patient group) are resuspended in sterile saline for intradermal injection.

Patients are administered AdVhAFP transduced DC injected ID in 0.1 ml normal saline in the flank region below the axillae or the groin. Patients are monitored for 2 hours post-immunization. Preferrably, patients receive pretreatment with 50 mg diphenhydramine and 650 mg of Tylenol™, both orally.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. An isolated peptide consisting of residues 137–145 of SEQ ID NO:2.

2. An isolated peptide consisting of residues 325–334 of SEQ ID NO:2.

* * * * *

SEQUENCE LISTING

<160> NUMBER OF SEQ ID NOS: 3

<210> SEQ ID NO 1
<211> LENGTH: 2032
<212> TYPE: DNA
<213> ORGANISM: Homo sapiens
<220> FEATURE:
<221> NAME/KEY: CDS
<222> LOCATION: (48)..(1874)
<223> OTHER INFORMATION:

<400> SEQUENCE: 1
tccatattgt gcttccacca ctgccaataa caaaataact agcaacc atg aag tgg    56
                                                   Met Lys Trp -continued

```
gtg gaa tca att ttt tta att ttc cta cta aat ttt act gaa tcc aga      104
Val Glu Ser Ile Phe Leu Ile Phe Leu Leu Asn Phe Thr Glu Ser Arg
    5               10                  15 aca ctg cat aga aat gaa tat gga ata gct tcc ata ttg gat tct tac      152
Thr Leu His Arg Asn Glu Tyr Gly Ile Ala Ser Ile Leu Asp Ser Tyr
 20              25                  30                  35 caa tgt act gca gag ata agt tta gct gac ctg gct acc ata ttt ttt      200
Gln Cys Thr Ala Glu Ile Ser Leu Ala Asp Leu Ala Thr Ile Phe Phe
             40                  45                  50 gcc cag ttt gtt caa gaa gcc act tac aag gaa gta agc aaa atg gtg      248
Ala Gln Phe Val Gln Glu Ala Thr Tyr Lys Glu Val Ser Lys Met Val
         55                  60                  65 aaa gat gca ttg act gca att gag aaa ccc act gga gat gaa cag tct      296
Lys Asp Ala Leu Thr Ala Ile Glu Lys Pro Thr Gly Asp Glu Gln Ser
         70                  75                  80 tca ggg tgt tta gaa aac cag cta cct gcc ttt ctg gaa gaa ctt tgc      344
Ser Gly Cys Leu Glu Asn Gln Leu Pro Ala Phe Leu Glu Glu Leu Cys
     85                  90                  95 cat gag aaa gaa att ttg gag aag tac gga cat tca gac tgc tgc agc      392
His Glu Lys Glu Ile Leu Glu Lys Tyr Gly His Ser Asp Cys Cys Ser
100                 105                 110                 115 caa agt gaa gag gga aga cat aac tgt ttt ctt gca cac aaa aag ccc      440
Gln Ser Glu Glu Gly Arg His Asn Cys Phe Leu Ala His Lys Lys Pro
                120                 125                 130 act cca gca tcg atc cca ctt ttc caa gtt cca gaa cct gtc aca agc      488
Thr Pro Ala Ser Ile Pro Leu Phe Gln Val Pro Glu Pro Val Thr Ser
            135                 140                 145 tgt gaa gca tat gaa gaa gac agg gag aca ttc atg aac aaa ttc att      536
Cys Glu Ala Tyr Glu Glu Asp Arg Glu Thr Phe Met Asn Lys Phe Ile
        150                 155                 160 tat gag ata gca aga agg cat ccc ttc ctg tat gca cct aca att ctt      584
Tyr Glu Ile Ala Arg Arg His Pro Phe Leu Tyr Ala Pro Thr Ile Leu
    165                 170                 175 ctt tgg gct gct cgc tat gac aaa ata att cca tct tgc tgc aaa gct      632
Leu Trp Ala Ala Arg Tyr Asp Lys Ile Ile Pro Ser Cys Cys Lys Ala
180                 185                 190                 195 gaa aat gca gtt gaa tgc ttc caa aca aag gca gca aca gtt aca aaa      680
Glu Asn Ala Val Glu Cys Phe Gln Thr Lys Ala Ala Thr Val Thr Lys
                200                 205                 210 gaa tta aga gaa agc agc ttg tta aat caa cat gca tgt gca gta atg      728
Glu Leu Arg Glu Ser Ser Leu Leu Asn Gln His Ala Cys Ala Val Met
            215                 220                 225 aaa aat ttt ggg acc cga act ttc caa gcc ata act gtt act aaa ctg      776
Lys Asn Phe Gly Thr Arg Thr Phe Gln Ala Ile Thr Val Thr Lys Leu
        230                 235                 240 agt cag aag ttt acc aaa gtt aat ttt act gaa atc cag aaa cta gtc      824
Ser Gln Lys Phe Thr Lys Val Asn Phe Thr Glu Ile Gln Lys Leu Val
    245                 250                 255 ctg gat gtg gcc cat gta cat gag cac tgt tgc aga gga gat gtg ctg      872
Leu Asp Val Ala His Val His Glu His Cys Cys Arg Gly Asp Val Leu
260                 265                 270                 275 gat tgt ctg cag gat ggg gaa aaa atc atg tcc tac ata tgt tct caa      920
Asp Cys Leu Gln Asp Gly Glu Lys Ile Met Ser Tyr Ile Cys Ser Gln
                280                 285                 290 caa gac act ctg tca aac aaa ata aca gaa tgc tgc aaa ctg acc acg      968
Gln Asp Thr Leu Ser Asn Lys Ile Thr Glu Cys Cys Lys Leu Thr Thr
            295                 300                 305 ctg gaa cgt ggt caa tgt ata att cat gca gaa aat gat gaa aaa cct     1016
```

```
                Leu Glu Arg Gly Gln Cys Ile Ile His Ala Glu Asn Asp Glu Lys Pro
                            310                 315                 320 gaa ggt cta tct cca aat cta aac agg ttt tta gga gat aga gat ttt           1064
Glu Gly Leu Ser Pro Asn Leu Asn Arg Phe Leu Gly Asp Arg Asp Phe
325                 330                 335 aac caa ttt tct tca ggg gaa aaa aat atc ttc ttg gca agt ttt gtt           1112
Asn Gln Phe Ser Ser Gly Glu Lys Asn Ile Phe Leu Ala Ser Phe Val
340                 345                 350                 355 cat gaa tat tca aga aga cat cct cag ctt gct gtc tca gta att cta           1160
His Glu Tyr Ser Arg Arg His Pro Gln Leu Ala Val Ser Val Ile Leu
                360                 365                 370 aga gtt gct aaa gga tac cag gag tta ttg gag aag tgt ttc cag act           1208
Arg Val Ala Lys Gly Tyr Gln Glu Leu Leu Glu Lys Cys Phe Gln Thr
            375                 380                 385 gaa aac cct ctt gaa tgc caa gat aaa gga gaa gaa tta cag aaa               1256
Glu Asn Pro Leu Glu Cys Gln Asp Lys Gly Glu Glu Leu Gln Lys
        390                 395                 400 tac atc cag gag agc caa gca ttg gca aag cga agc tgc ggc ctc ttc           1304
Tyr Ile Gln Glu Ser Gln Ala Leu Ala Lys Arg Ser Cys Gly Leu Phe
    405                 410                 415 cag aaa cta gga gaa tat tac tta caa aat gcg ttt ctc gtt gct tac           1352
Gln Lys Leu Gly Glu Tyr Tyr Leu Gln Asn Ala Phe Leu Val Ala Tyr
420                 425                 430                 435 aca aag aaa gcc ccc cag ctg acc tcg tcg gag ctg atg gcc atc acc           1400
Thr Lys Lys Ala Pro Gln Leu Thr Ser Ser Glu Leu Met Ala Ile Thr
                440                 445                 450 aga aaa atg gca gcc aca gca gcc act tgt tgc caa ctc agt gag gac           1448
Arg Lys Met Ala Ala Thr Ala Ala Thr Cys Cys Gln Leu Ser Glu Asp
            455                 460                 465 aaa cta ttg gcc tgt ggc gag gga gcg gct gac att att atc gga cac           1496
Lys Leu Leu Ala Cys Gly Glu Gly Ala Ala Asp Ile Ile Ile Gly His
        470                 475                 480 tta tgt atc aga cat gaa atg act cca gta aac cct ggt gtt ggc cag           1544
Leu Cys Ile Arg His Glu Met Thr Pro Val Asn Pro Gly Val Gly Gln
    485                 490                 495 tgc tgc act tct tca tat gcc aac agg agg cca tgc ttc agc agc ttg           1592
Cys Cys Thr Ser Ser Tyr Ala Asn Arg Arg Pro Cys Phe Ser Ser Leu
500                 505                 510                 515 gtg gtg gat gaa aca tat gtc cct cct gca ttc tct gat gac aag ttc           1640
Val Val Asp Glu Thr Tyr Val Pro Pro Ala Phe Ser Asp Asp Lys Phe
                520                 525                 530 att ttc cat aag gat ctg tgc caa gct cag ggt gta gcg ctg caa acg           1688
Ile Phe His Lys Asp Leu Cys Gln Ala Gln Gly Val Ala Leu Gln Thr
            535                 540                 545 atg aag caa gag ttt ctc att aac ctt gtg aag caa aag cca caa ata           1736
Met Lys Gln Glu Phe Leu Ile Asn Leu Val Lys Gln Lys Pro Gln Ile
        550                 555                 560 aca gag gaa caa ctt gag gct gtc att gca gat ttc tca ggc ctg ttg           1784
Thr Glu Glu Gln Leu Glu Ala Val Ile Ala Asp Phe Ser Gly Leu Leu
    565                 570                 575 gag aaa tgc tgc caa ggc cag gaa cag gaa gtc tgc ttt gct gaa gag           1832
Glu Lys Cys Cys Gln Gly Gln Glu Gln Glu Val Cys Phe Ala Glu Glu
580                 585                 590                 595 gga caa aaa ctg att tca aaa act cgt gct gct ttg gga gtt                   1874
Gly Gln Lys Leu Ile Ser Lys Thr Arg Ala Ala Leu Gly Val
                600                 605 taaattactt cagggaaga gaagacaaaa cgagtctttc attcggtgtg aactttctc           1934 tttaatttta actgatttaa cacttttgt gaattaatga aatgataaag acttttatgt          1994
```

```
gagatttcct tatcacagaa ataaaatatc tccaaatg                                    2032
```

<210> SEQ ID NO 2
<211> LENGTH: 609
<212> TYPE: PRT
<213> ORGANISM: Homo sapiens

<400> SEQUENCE: 2

```
Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365
```

```
Val Ile Leu Arg Val Ala Lys Gly Tyr Gln Glu Leu Leu Glu Lys Cys
    370             375             380

Phe Gln Thr Glu Asn Pro Leu Glu Cys Gln Asp Lys Gly Glu Glu Glu
385                 390             395                 400

Leu Gln Lys Tyr Ile Gln Glu Ser Gln Ala Leu Ala Lys Arg Ser Cys
                405             410             415

Gly Leu Phe Gln Lys Leu Gly Glu Tyr Tyr Leu Gln Asn Ala Phe Leu
            420             425             430

Val Ala Tyr Thr Lys Lys Ala Pro Gln Leu Thr Ser Ser Glu Leu Met
            435             440             445

Ala Ile Thr Arg Lys Met Ala Ala Thr Ala Ala Thr Cys Cys Gln Leu
    450             455             460

Ser Glu Asp Lys Leu Leu Ala Cys Gly Glu Gly Ala Ala Asp Ile Ile
465             470             475             480

Ile Gly His Leu Cys Ile Arg His Glu Met Thr Pro Val Asn Pro Gly
            485             490             495

Val Gly Gln Cys Cys Thr Ser Ser Tyr Ala Asn Arg Arg Pro Cys Phe
            500             505             510

Ser Ser Leu Val Val Asp Glu Thr Tyr Val Pro Pro Ala Phe Ser Asp
            515             520             525

Asp Lys Phe Ile Phe His Lys Asp Leu Cys Gln Ala Gln Gly Val Ala
        530             535             540

Leu Gln Thr Met Lys Gln Glu Phe Leu Ile Asn Leu Val Lys Gln Lys
545             550             555             560

Pro Gln Ile Thr Glu Glu Gln Leu Glu Ala Val Ile Ala Asp Phe Ser
                565             570             575

Gly Leu Leu Glu Lys Cys Cys Gln Gly Gln Glu Gln Glu Val Cys Phe
            580             585             590

Ala Glu Glu Gly Gln Lys Leu Ile Ser Lys Thr Arg Ala Ala Leu Gly
                595             600             605

Val

<210> SEQ ID NO 3
<211> LENGTH: 609
<212> TYPE: PRT
<213> ORGANISM: Homo sapiens

<400> SEQUENCE: 3

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65              70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125
```

```
Lys Lys Pro Thr Pro Ala Ser Ile Pro Leu Phe Gln Val Pro Glu Pro
130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
                180                 185                 190

Cys Lys Ala Glu Asn Ala Val Glu Cys Phe Gln Thr Lys Ala Ala Thr
            195                 200                 205

Val Thr Lys Glu Leu Arg Glu Ser Ser Leu Leu Asn Gln His Ala Cys
210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
                260                 265                 270

Asp Val Leu Asp Cys Leu Gln Asp Gly Glu Lys Ile Met Ser Tyr Ile
                275                 280                 285

Cys Ser Gln Gln Asp Thr Leu Ser Asn Lys Ile Thr Glu Cys Cys Lys
            290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
                340                 345                 350

Ser Phe Val His Glu Tyr Ser Arg Arg His Pro Gln Leu Ala Val Ser
            355                 360                 365

Val Ile Leu Arg Val Ala Lys Gly Tyr Gln Glu Leu Leu Glu Lys Cys
370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
                420                 425                 430

Val Ala Tyr Thr Lys Lys Ala Pro Gln Leu Thr Ser Ser Glu Leu Met
            435                 440                 445

Ala Ile Thr Arg Lys Met Ala Ala Thr Ala Ala Thr Cys Cys Gln Leu
450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
            515                 520                 525

Asp Lys Phe Ile Phe His Lys Asp Leu Cys Gln Ala Gln Gly Val Ala
530                 535                 540

Leu Gln Thr Met Lys Gln Glu Phe Leu Ile Asn Leu Val Lys Gln Lys
```

-continued

```
545                 550                 555                 560
Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
        595                 600                 605

Val
```